(12) United States Patent
Ewing

(10) Patent No.: US 6,521,613 B2
(45) Date of Patent: Feb. 18, 2003

(54) LACTAM COMPOUNDS FOR PENETRATION ENHANCEMENT

(75) Inventor: Gary Ewing, Kalamazoo, MI (US)

(73) Assignee: Allergan, Inc., Irvine, CA (US)

( * ) Notice: Subject to any disclaimer, the term of this patent is extended or adjusted under 35 U.S.C. 154(b) by 0 days.

(21) Appl. No.: 09/829,641

(22) Filed: Apr. 10, 2001

(65) Prior Publication Data
US 2002/0193449 A1 Dec. 19, 2002

(51) Int. Cl.[7] ............... A61K 31/55; C07D 223/10; C07D 201/00
(52) U.S. Cl. ............ 514/212.03; 540/487; 540/531; 540/533
(58) Field of Search ................. 540/487, 531, 540/533; 514/212.03

(56) References Cited

U.S. PATENT DOCUMENTS

| | | | |
|---|---|---|---|
| 3,975,377 A | 8/1976 | Poulain | 260/239.3 |
| 3,988,318 A | 10/1976 | Copes et al. | 260/239.3 |
| 4,246,397 A | 1/1981 | Choi | 528/380 |
| 4,743,588 A | 5/1988 | Mirejovsky et al. | 514/24 |
| 5,206,386 A | 4/1993 | Narayanan et al. | 548/551 |
| 5,280,092 A | 1/1994 | Chuang | 526/201 |
| 5,294,644 A | 3/1994 | Login et al. | 514/698 |
| 5,512,293 A | 4/1996 | Landrau et al. | 424/449 |
| 5,695,779 A | 12/1997 | Mori | 424/448 |
| 6,004,578 A | 12/1999 | Lee et al. | 424/448 |

FOREIGN PATENT DOCUMENTS

| | | |
|---|---|---|
| JP | 43026176 | 11/1968 |
| JP | 51004317 | 1/1976 |
| JP | 51004319 | 1/1976 |

*Primary Examiner*—Bruck Kifle
(74) *Attorney, Agent, or Firm*—Stout, Uxa, Buyan & Mullins, LLP; Frank J. Uxa

(57) ABSTRACT

Compounds, compositions and methods are disclosed useful for enhancing penetration of a pharmacologically active substances across skin or tissue membranes. Compounds for use in such compositions and methods are highly water-soluble N-substituted polyalkylene oxide derivatives of cyclic amides. A compound of the invention has the structural formula:

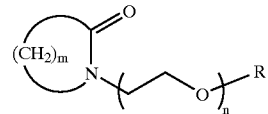

wherein m is an integer from 2 to about 6, n is an integer from 1 to about 8, and R is hydrogen, trimethylsilyl or lower alkyl.

21 Claims, No Drawings

LACTAM COMPOUNDS FOR PENETRATION ENHANCEMENT

BACKGROUND OF THE INVENTION

The present invention relates to compositions, components and methods useful in delivering pharmacologically active substances. More particularly, the invention relates to such compounds, compositions and methods for enhancing the penetration or transport of pharmacologically active substances transdermally, that is through the skin, or through a membrane, for example, the cornea and other tissue membranes. The invention also relates to methods of making such compounds.

There continues to be considerable interest in developing pharmaceutical compositions that can be administered topically either for local or systemic benefit. The skin is the largest and most accessible organ of the body, which makes it a particularly attractive target for drug delivery. With regard to systemic uses, the exposed surfaces of the body potentially offer pharmacological advantages, such as avoiding a first pass through the liver, affording greater control over dosage so as to permit the use of drugs having a relatively small therapeutic index, and avoiding side effects otherwise incurred through gastrointestinal delivery.

A principal obstacle to adopting wider use of topical delivery protocols is the barrier to drug penetration presented by external tissues, particularly in the outermost layer of dead keratinized cells. Use of increased dosages in order to overcome the barrier can have unacceptable side effects. A popular approach to penetrating this barrier has been with the use of surface active agents. However, these substances frequently damage the barrier tissue and often show only slight or moderate penetration enhancement. Organic solvents, such as dimethylsulfoxide, dimethylacetamide, and pyrrolidone have also been studied. However, these compounds are often systemically distributed in a short period of time and cause undesirable side effects.

A variety of penetration enhancement vehicles have been proposed over the years. These include amides of heterocyclic amines as described by Mirejovsky et al U.S. Pat. No. 4,743,588, polymers containing heterocyclic groups as described by Choi U.S. Pat. No. 4,246,397, and copolymers of polyvinyl acetate and polyvinyl pyrrolidone as described by Landrau et al U.S. Pat. No. 5,512,293. Permeation enhancers based on the monoalkylethers and alkyl or aryl esters of polyethylene glycol have been proposed, for example, by Lee et al. U.S. Pat. No. 6,004,578.

A further class of compounds studied for their solubilizing properties are the cyclic amides, also referred to as lactams. The lactams are particularly interesting because of the relatively high dipole moment possessed by these compounds. For instance, Login et al U.S. Pat. No. 5,294,644 disclose N-alkyl substituted lactams for use as surfactants. Such compounds can be made by reacting an alkali metal lactamate with an alkyl halide, as disclosed by Poulain U.S. Pat. No. 3,975,377, or by reacting a lactam with ethyleneoxide in the presence of a suitable basic catalyst, as described by Senda et al Japanese Patent 43-26176. N-alkyl substituted lactams, wherein the N-alkyl group contains a hydrolyzable organic acid moiety such as salicylic acid, have been proposed as carriers for biologically active agents by Narayanan et al U.S. Pat. No. 5,206,386. It has been suggested by Copes et al U.S. Pat. No. 3,988,318 that under some conditions, N-alkyl lactams can form complexes with phenols for use as germicides, antiseptic soaps, and emollients.

Further, an emulsifier comprising a mixture of an N-alkyl lactam and a non-ionic surfactant, such as a polyethylene glycol alkyl ester, has been proposed by Chuang U.S. Pat. No. 5,280,092.

There continues to be a need to provide compounds, compositions and methods useful to increase the effectiveness of topical administration of pharmaceuticals.

SUMMARY OF THE INVENTION

The present invention is directed to compounds, compositions, and methods for enhancing the transdermal or transmembrane transport of pharmacologically active substances. The invention also provides methods for making the present compounds. In short, the present invention is useful in the topical administration of pharmacologically active substances, and preferably increases or enhances the effectiveness of such topical administration. Advantageously, the present compounds, compositions and methods of use provide local and/or systemic benefits from pharmaceuticals, because of, for example, enhanced dosage control and reduced side effects. The methods of making the present compounds are relatively straightforward and cost effective to practice.

The present compounds contain a N-alkyl lactam moiety, and preferably are highly water soluble. Conventional N-alkyl lactams are not substantially soluble in water. However, the compounds of the present invention include a strongly hydrophilic non-ionic portion or tail bonded to the amide nitrogen atom of the lactam. Representative hydrophilic groups include polyalkyleneoxy chains, such as polyethylene glycol (PEG), which can have a terminal hydroxyl group or a terminal alkyl group.

In one broad aspect of the present invention, compounds are provided having a chemical formula as shown below:

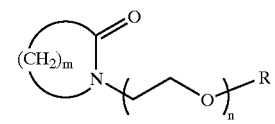

wherein m is an integer in a range of 2 to about 6, n is an integer in a range of 1 to about 8, and R is selected from hydrogen, trimethylsilyl, or lower alkyl, preferably alkyl having 1 to 6 carbon atoms. In one embodiment, m preferably is 3.

In another broad aspect of the present invention, methods for making the present compounds are provided. In one embodiment, methods for making the present compounds in which R is selected from trimethylsilyl and lower alkyl comprise deprotonating a lactam and reacting the deprotonated lactam with a suitable polyalkyleneoxide having or including a leaving group to afford or yield the present compound. Although the polyalkyleneoxide may include any suitable leaving group, in one embodiment the leaving group is tosylate. The present trimethylsilyl (TMS) derivative can be employed as a convenient precursor for making the terminal hydroxyl derivative. For example, the TMS derivative can be hydrolyzed to generate the corresponding compound with a terminal hydroxyl group.

In further broad aspects of the present invention, compositions and methods for enhancing transdermal or transmembrane transport of pharmacologically active substances (medications or drugs) are provided. Such compositions comprise an effective amount of a pharmacologically active substance and at least one compound of the present invention in which R is selected from hydrogen and lower alkyl. The at least one compound is present in an amount effective to enhance the transdermal or transmembrane transport of the active substance in a similar composition without the at least one compound. The at least one compound may be present in any suitable, effective concentration, for example, effective to enhance transdermal and/or transmembrane transport of the active substance. The at least one compound preferably is present in the composition in an amount in a range of about 0.1% to about 50% by weight of the composition. Any suitable pharmacologically active substance or substances may be employed in the present compositions. Such substances preferably are pharmacologically effective when administrated transdermally and/or when administered by being passed through a membrane, for example, a tissue membrane.

Without wishing to be bound by any particular theory of operation, it is believed that the hydrophilic polyalkyleneoxy portion or tail bonded, for example, covalently bonded, to the nitrogen atom of the lactam increases the water solubility of the lactam group. The pharmacologically active substance, which may form one or more stable or transient complexes with the highly polar lactam moiety, in combination with the modified lactam shows enhanced penetration or transdermal or transmembrane transport when compared with a similar composition without the lactam moiety.

In yet another broad aspect of the present invention, methods for administering pharmacologically active substances are provided. Such methods comprise topically administering to a human or animal a therapeutically effective amount of a composition, as described elsewhere herein, in accordance with the present invention.

Any and all features described herein and combinations of such features are included within the scope of the present invention provided that the features of any such combination are not mutually inconsistent.

These and other aspects and advantages of the present invention are set forth in the following, detailed description and claims.

DETAILED DESCRIPTION OF THE INVENTION

The present invention is directed to compounds, and compositions and methods for enhancing transdermal and/or transmembrane transport of pharmacologically active substances, e.g., through enhanced transdermal and/or transmembrane penetration. The active substance can have local or systemic benefit, and is not limited to any particular mechanism of action.

Compounds of the present invention have a structural formula as shown hereinbelow:

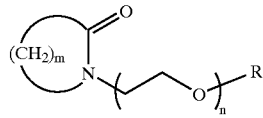

wherein m is an integer from 2 to about 6, n is an integer from 1 to about 8, and R is selected from hydrogen, trimethylsilyl, and lower alkyl. As used herein, "lower alkyl" refers to linear, branched or cyclic alkyl groups preferably containing 1 to 6 carbon atoms, more preferably 1 to 4 carbon atoms.

Compounds of the present invention are referred to herein generally as N-substituted lactams, which are cyclic or internal amides. Also, the compounds can have trivial names according to the number of carbon atoms in the heterocyclic ring. For instance, 4-membered lactam rings are referred to as 2-azetidinones (β-propiolactams), 5-membered rings as 2-pyrrolidinones or 2-pyrrolidones (γ-butanolactams), 6-membered rings as 2-piperidones (δ-valerolactams), 7-membered rings as 2-oxohexamethyleneimines (ε-caprolactams), and so forth.

Synthesis of the compounds of the present invention typically proceeds by converting the amide of the lactam into a negatively charged nucleophile. This is conveniently performed by treating the lactam with a suitable metal hydride in aprotic solvent with the elimination of hydrogen gas and the production of a deprotonated lactam. Exemplary hydrides include, without limitation, sodium hydride, lithium aluminum hydride, sodium borohydride, diisobutylaluminum hydride and the like and mixtures thereof. The amido anion is then reacted with a selected polyalkyleneoxide moiety that has been activated with a suitable leaving group. The p-toluenesulfonyl (tosyl) group is conveniently employed for this purpose by reacting p-toluenesulfonyl chloride with the free hydroxyl group of the polymeric alkyleneoxide in the presence of a dry basic solvent, such as pyridine. Reaction of the deprotonated lactam with the activated polyalkyleneoxide compound affords or provides the desired N-substituted lactam in accordance with the present invention. These reactions are illustrated in the following scheme:

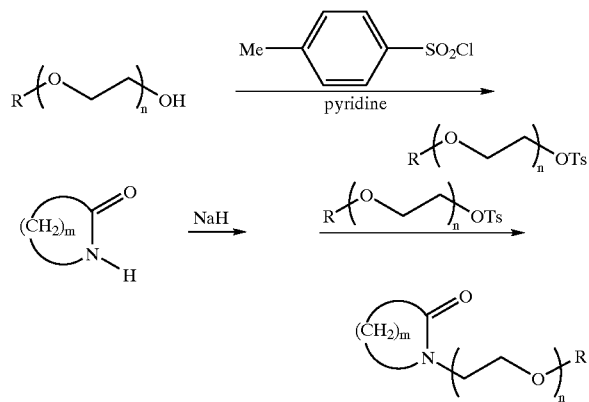

In the above reactions, m is an integer in a range of 2 to 6, n is an integer in a range of 1 to 8, and R is trimethylsilyl (TMS) or a lower alkyl group. The TMS derivative of the polyol can be prepared by direct reaction of the polyol with trimethylsilyl chloride in the presence of an amine solvent. After coupling the polyol moiety to the lactam, it is frequently desired to hydrolyze the TMS group, thereby generating a free hydroxyl terminus, e.g., for further reaction or to increase water solubility. Cleavage of the TMS group from the N-substituted lactam compound is conveniently performed by hydrolyzing it in the presence of a fluoride catalyst. Exemplary fluoride catalysts include aqueous HF, boron trifluoride and the like and mixture thereof.

Whenever R equals H in the above formula, the compound can be further reacted with another compound as desired. For instance, the N-substituted lactam can be conjugated to a pharmacologically active agent bearing a carboxylic acid group, whereby the lactam moiety can be considered as a carrier for the active agent. The molecule cleaves in vivo under physiologic conditions to release the active agent for local or systemic benefit near or within target tissues.

The ability of compounds of the present invention to enhance transdermal or transmembrane or transport penetration of pharmacologically active agents having limited water solubilities provides advantageous benefits. For example, the compounds prednisolone, guanethidine, and flurbiprofen have wide-ranging structural differences. Nevertheless, compounds of the present invention have been found to be effective to enhance transmembrane, in particular transcorneal, penetration of each of these widely differing compounds.

Accordingly, a further aspect of the invention is directed to methods and compositions for enhancing penetration of a pharmacologically active agent, e.g., across skin or tissue membrane barriers. Such a pharmaceutical composition comprises at least one of the compounds of the present invention and the pharmacologically active agent, for example, admixed with or chemically, e.g., covalently, bonded to the active component. The composition comprises an amount of at least one of the compounds of the present invention effective to enhance the transdermal or transmembrane transport of the active agent relative to the transdermal or transmembrane transport of an identical active agent in a similar composition without the at least one compound. Preferably, the at least one compound of the present invention is present in the compositions in an amount in a range of about 0.1% to about 50%, more preferably about 0.5% to about 40%, by weight of the composition.

The at least one compound of the invention can be administered separately from the active agent. More typically, however, the compound or compounds of the present invention are combined with the pharmacologically active substance or substances in a single composition which is administered to the patient, as desired.

It is to be appreciated that suitable polyalkyleneoxides may have a range of molecular weights, which upon synthesis afford lactam compounds having a range of molecular weights as well. For example, commercially available polyalkyleneoxides often have a range of molecular weights in a single product. Conveniently, the mixture of compounds in accordance with the present invention afforded because of such different molecular weight polyalkyleneoxides need not be separated before use.

The present compositions can be applied, for example, topically applied or administered, to a target surface directly in any suitable form, for example, as a liquid solution or suspension or dispersion, a gel, a paste, a transdermal patch or the like. Use of a transdermal patch is recommended whenever a significant likelihood exists of the composition drying or rubbing off of the exposed surface.

Methods for enhancing penetration of pharmacologically active substances comprise topically administering to a human or animal subject a composition in accordance with the present invention. Suitable dosages of pharmacologically active substance or substances, as well as of the compound or compounds of the present invention, depend upon their relative therapeutic indices and can be determined by a physician or the skilled practitioner. The active substances can have a wide range of chemical structures and pharmacological activities, e.g., such as analgesics, corticosteroids, anti-hypertensives and this like and mixtures thereof.

The pharmacologically active substances useful in the present invention preferably are pharmacologically effective when administered transdermally or by being passed through a membrane, for example, a tissue membrane, more preferably by being topically administered.

As used herein, the term "pharmacologically active substance" refers to a broad class of chemical and therapeutic agents sufficiently potent so as to be capable of being delivered through the skin or other membrane, e.g, transmembrane, in sufficient quantity to produce the desired therapeutic effect. This characterization includes therapeutic agents or substances in all of the major therapeutic categories, including but not limited to anti-infectives, such as antibiotics and antiviral agents, analgesics, and analgesic combinations, anorexics, anthelmintics, anti-arthritics, anti-asthma agents, anti-convulsants, antidepressants, anti-diabetic agents, anti-diarrheals, antihistamines, anti-inflammatory agents, anti-migraine preparations, anti-motion sickness, anti-nauseants, anti-neoplastics, anti-parkinsonism drugs, anti-pruritics, antipsychotics, antipyretics, anti-spasmodics including gastrointestinal and urinary anti-spasmodics, anti-cholinergics, sympathomimetics, xanthine derivatives, cardiovascular preparations including calcium channel blockers, beta-blockers, anti-arrhythmics, anti-hypertensives, diuretics and vasodilators including general, coronary, peripheral and cerebral, central nervous system stimulants, cough and cold preparations, decongestants, diagnostics, hormones, hypnotics, immunosuppressives, muscle relaxants, parasympatholytics, parasympathomimetics, psychostimulants, sedatives and tranquilizers and the like and mixtures and combinations thereof.

The compositions of the present invention can be formulated in a variety of dosage forms for topical application. A wide variety of dermatologically acceptable inert carriers well known to the art may be employed. The topical compositions may include liquids, creams, lotions, ointments, gels, sprays, aerosols, skin patches, and the like. Typical inert carriers could be, for example, water, ethyl alcohol, polyvinyl pyrrolidone, propylene glycol, mineral oil, stearyl alcohol, spermaceti, gel-producing substances and the like and mixtures thereof.

Many, if not all, of the above dosage forms and carriers are well known to the cosmetic and pharmaceutical art. The choice of dosage form is not critical to the present invention, for example, to the efficacy of the penetration enhancing compound of the invention or to the pharmacologically active substance.

Of course, the compositions of the present invention may include additional components, for example, conventional components, in amounts effective to provide desired benefits or properties to the compositions.

The following non-limiting examples illustrate certain aspects of the present invention.

EXAMPLE 1

Preparation of Triethyleneoxyethylether P-toluenesulfonate (I)

To a solution of dry pyridine (15 mL) and p-toluenesulfonyl chloride (25.2 g, 132 mmol) in dry $CH_2Cl_2$ (200 mL) at 0° C. is added a solution of triethyleneglycol monoethylether (21.4 g, 120 mmol) in dry $CH_2Cl_2$ (25 mL) dropwise over 0.5 hour. After rinsing the addition funnel with $CH_2Cl_2$ (10 mL), the mixture is stirred for 1 hour at 0° C. and then placed into a refrigerator overnight.

The mixture is poured into a separatory funnel containing 200 mL ice cold dilute HCl solution (20 mL conc. HCl, 80 mL water, and 200 mL ice cubes). After washing, the organic phase is washed with saturated $NaHCO_3$ solution (2×100 mL), dried over $MgSO_4$ for 1 hour and rotary evaporated to give compound I as a clear oil (41.8 g). Thin layer chromatography ($SiO_2/CH_2Cl_2$) indicates that the oil is likely a mixture of starting materials and desired product. Repetition of the reaction at room temperature and higher solution concentrations gives similar results.

EXAMPLE 2

Preparation of N-triethoxyethylether Caprolactam (II)

A 50% oil dispersion of NaH (5.76 g) is placed in a 3-neck round bottom flask (250 mL) and washed with hexane under dry nitrogen. The hexane is decanted three times and the last traces are removed by vacuum. DMSO (50 mL) is added and stirred until gas evolution ceased. To this mixture is added caprolactam (13.02 g, 115 mmol) in dry DMSO (50 mL). The mixture is stirred overnight and an additional 50 mL of DMSO is added to aid control of foaming. The tosylate oil (compound I, 41 g) from Example 1 is added dropwise with the reaction being slightly exothermic. After completion of addition, the mixture is warmed to 40–50° C. for 2 hours. The reaction mixture is worked up with $CH_2Cl_2$ and water, then the organic phase is dried over $MgSO_4$ and rotary evaporated to give a reddish brown oil. Flash distillation removes most of the DMSO and the highly colored material remaining is distilled a second time using nitrogen ebullition to give compound II as an oil (19.7 g). A third fractional distillation gives more compound II (17.0 g). Compound II: bp=138° C. @ 3 μm Hg, $\eta_{25}$=1.4690, $\lambda_{max}$=222 nm (ε=812, methanol)·$^1$H NMR=1.20 (t, J=9 Hz, 3H), 1.69 (bs, 6H), 2.52 (m, 2H), 3.30–3.65 (m, 16H).

EXAMPLE 3

Preparation of Triethyleneoxy(Trimethylsilyl)ether P-toluenesulfonate (III)

To a solution of dry pyridine and trimethylsilyl chloride in dry $CH_2Cl_2$ at 0° C. in an addition funnel is added a solution of triethyleneglycol in dry $CH_2Cl_2$ dropwise over time. After rinsing the addition funnel with $CH_2Cl_2$ the mixture is stirred for a period of time at 0° C. The reaction product is further treated with p-toluenesulfonyl chloride as described above in Example 1 to give compound III.

EXAMPLE 4

Preparation of N-triethoxy(Trimethylsilyl)Ether Caprolactam (IV) and N-triethyleneglycol Caprolactam (V)

The tosylate oil of Example 3 (compound III) is reacted with caprolactam as described in Example 2 to give compound IV. Unisolated compound IV is hydrolyzed in a suitable solvent in the presence of an effective fluoride catalyst to give compound V.

EXAMPLE 5

Penetration Enhancement Testing

Permeation efficiencies are determined by measuring the rate of diffusion of drug between posterior and anterior chambers separated by rabbit cornea. Suitable test drugs include prednisolone, guanethidine, and flurbiprofen. Compounds II and V, described in Examples 2 and 4 above, are tested penetration enhancers. Water, acetone, ethanol, and GBR (glutathione-buffered Ringer's solution) are convenient vehicles used alone or in combination together with the test drugs and the proposed penetration enhancers. The relative rates of diffusion can be determined indirectly by measuring pH versus time in the respective chambers, or by HPLC.

Results of this testing show that each of the present compounds II and V provide enhanced penetration or permeation of all of the test drugs relative to similar compositions without the present compounds.

EXAMPLES 6 TO 10

The following compositions in accordance with the present invention are prepared by blending together the components indicated.

EXAMPLE 6

SOLUTION

| Ingredients | Percent W/W |
| --- | --- |
| Hydrocortisone | 1 |
| Compound V | 5 |
| Propylene Glycol | 15 |
| Ethanol q.s. | 100 |

EXAMPLE 7

CREAM

| Ingredients | Percent W/W |
| --- | --- |
| Trifluorothymidine | 1.0 |
| Compound V | 10.0 |
| Emulsifying Wax | 15.0 |
| Light Mineral Oil | 5.0 |
| Benzyl Alcohol | 0.5 |
| Imidazolidinyl Urea | 0.3 |
| Purified Water q.s. | 100.0 |

EXAMPLE 8

OINTMENT

| Ingredients | Percent W/W |
| --- | --- |
| Polyethylene Glycol 4000 | 33.0 |
| Cetyl Alcohol | 5.0 |
| Polysorbate 60 | 5.0 |
| Isopropyl Myristate | 5.0 |
| Propylene Glycol | 10.0 |
| Polyethylene Glycol 300 | 21.0 |
| Cimetidine base | 1.0 |
| Compound V | 20.0 |

EXAMPLE 9

GEL

| Ingredients | Percent W/W |
| --- | --- |
| Hydrocortisone | 1.0 |
| Compound V | 5.0 |
| Propylene Glycol | 10.0 |
| Isopropyl Myristate | 10.0 |
| Carbomer 940 | 3.5 |
| Citric Acid, Monohydrate | 0.1 |
| Alcohol q.s. | 100.0 |

EXAMPLE 10

| LOTION | |
|---|---|
| Ingredients | Percent W/W |
| Trifluorothymidine | 2.0 |
| Compound V | 1.0 |
| Imidazolidinyl Urea | 0.3 |
| Benzyl Alcohol | 0.5 |
| PEG-24 Hydrogenated Lanolin | 1.0 |
| Purified Water q.s. | 100.0 |

While this invention has been described with respect to various specific examples and embodiments, it is to be understood that the invention is not limited thereto and that it can be variously practiced within the scope of the following claims.

What is claimed is:

1. A compound having the formula:

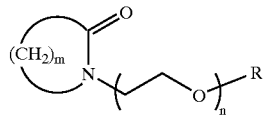

wherein m is an integer equal to 5, n is an integer in a range of 1 to 8, and R is selected from the group consisting of trimethylsilyl and lower alkyl having 1 to 6 carbon atoms.

2. The compound of claim 1, wherein R is trimethylsilyl.

3. The compound of claim 1, wherein R is lower alkyl having 1 to 6 carbon atoms.

4. The compound of claim 1, wherein R is lower alkyl having 1 to 4 carbon atoms.

5. A method of making a compound having the formula:

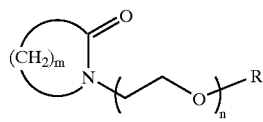

wherein m is an integer equal to 5, n is an integer in a range of 1 to 8, and R is selected from the group consisting of trimethylsilyl and lower alkyl having 1 to 6 carbon atoms, the method comprising deprotonating a lactam to produce a deprotonated lactam and reacting the deprotonated lactam with a polyalkyleneoxide including a leaving group to afford said compound.

6. The method of claim 5, wherein the leaving group is tosylate.

7. The method of claim 5, wherein R is trimethylsilyl, the method further comprising hydrolyzing said compound to generate a terminal hydroxyl group.

8. A composition for enhancing transdermal or transmembrane transport of a pharmacologically active substance, the composition comprising a pharmacologically active substance in an amount effective to provide a desired therapeutic effect when administered to a patient transdermally or by being passed through a membrane, and at least one compound having the formula:

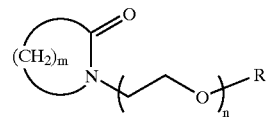

wherein m is an integer equal to 5, n is an integer from 1 to 8, and R is selected from the group consisting of hydrogen, trimethylsilyl and lower alkyl having 1 to 6 carbon atoms, the at least one compound being present in an amount effective to enhance the transdermal or transmembrane transport of said active substance relative to the transdermal or transmembrane transport of an identical active substance in a similar composition without the at least one compound.

9. The composition of claim 8, wherein the at least one compound is present in an amount in a range of about 0.1% to about 50% by weight of the composition.

10. The composition of claim 8, wherein R is hydrogen.

11. The composition of claim 8, wherein R is trimethylsilyl.

12. The composition of claim 8, wherein R is lower alkyl having 1 to 4 carbon atoms.

13. The composition of claim 8, wherein the active substance is present in an amount effective to provide a desired therapeutic effect when administered transdermally.

14. The composition of claim 8, wherein the active substance is present in an amount effective to provide a desired therapeutic effect when administered by being passed through a membrane.

15. A method for administering a pharmacologically active substance comprising topically administering to a human or animal a therapeutically effective amount of a composition comprising a pharmacologically active substance present in an amount effective to provide a desired therapeutic effective when administered topically to a human or animal and at least one compound having the formula:

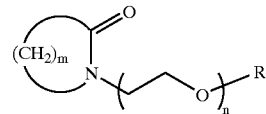

wherein m is an integer equal to 5, n is an integer from 1 to 8, and R is selected from the group consisting of hydrogen, trimethylsilyl and lower alkyl having 1 to 6 carbon atoms, said at least one compound being present in an amount effective to enhance the transdermal or transmembrane transport of said active substance relative to the transdermal or transmembrane transport of an identical active substance in a similar composition without the at least one compound.

16. The method of claim 15, wherein the at least one compound is present in an amount in a range of about 0.5% to about 40% by weight of the composition.

17. The method of claim 15, wherein R is hydrogen.

18. The method of claim 15, wherein R is trimethylsilyl.

19. The method of claim 15, wherein R is lower alkyl having 1 to 4 carbon atoms.

20. The method of claim 15, wherein the active substance is pharmacologically effective when administered transdermally.

21. The method of claim 15, wherein the active substance is pharmacologically effective when administered by being passed through a membrane.

* * * * *